United States Patent [19]

Levandoski

[11] Patent Number: 5,020,993
[45] Date of Patent: Jun. 4, 1991

[54] DENTAL ARTICULATOR

[76] Inventor: Ronald R. Levandoski, 1103 Powell Ave., Erie, Pa. 16505

[21] Appl. No.: 460,041

[22] Filed: Jan. 2, 1990

[51] Int. Cl.⁵ ............................................. A61C 11/00
[52] U.S. Cl. .................................... 433/65; 433/57; 433/63
[58] Field of Search ................... 433/65, 54, 55, 56, 433/57, 58, 59, 61, 62, 63, 64, 67, 68, 69

[56] References Cited

U.S. PATENT DOCUMENTS

| | | | |
|---|---|---|---|
| 1,033,562 | 7/1912 | Eltner | 433/56 |
| 2,617,195 | 11/1952 | Perkell et al. | 433/65 |
| 3,160,955 | 12/1964 | DePietro | 433/56 |
| 3,206,852 | 9/1965 | Swanson | 433/56 |
| 3,409,986 | 11/1968 | Freeman | 433/55 |
| 3,478,431 | 11/1969 | DePietro | 433/57 |
| 3,590,487 | 7/1971 | Guichet | 433/62 |
| 4,265,620 | 5/1981 | Moro et al. | 433/69 |
| 4,299,570 | 11/1981 | Yogosawa | 433/62 |
| 4,330,276 | 5/1982 | Becker et al. | 433/55 |
| 4,468,198 | 8/1984 | Kataoka et al. | 433/65 |
| 4,500,290 | 2/1985 | Anderson | 433/65 |
| 4,668,189 | 5/1987 | Levandoski | 433/55 |

*Primary Examiner*—John J. Wilson
*Attorney, Agent, or Firm*—Charles L. Lovercheck; Wayne L. Lovercheck; Dale Lovercheck

[57] ABSTRACT

An articulator having an upper frame having an upper arm and a lower frame having a lower arm. A pivot is provided on the upper arm swingably supporting the upper frame on the lower frame. Adjusting mechanism is provided for adjusting the upper arm relative to the lower arm so that a casting supported on the upper arm can be rotated relative to the lower arm or tilted up and down, forward and laterally, as well as swinging the upper casting relative to the lower casting. The dental articulator simulates the operation of human jaws for use in the manufacture of false teeth. An upper frame representing the upper jaw is mounted to a lower frame by a pair of ball and socket joints which may be adjusted to approximate a specific patient's jaw hinge. The adjusting mechanism can include a computer controlled motor for adjusting the upper arm relative to the lower arm in accordance with X-ray data of a patient's jaw structure.

23 Claims, 10 Drawing Sheets

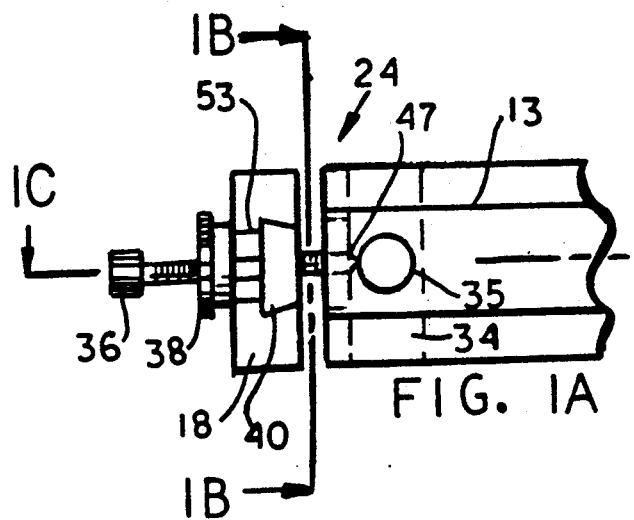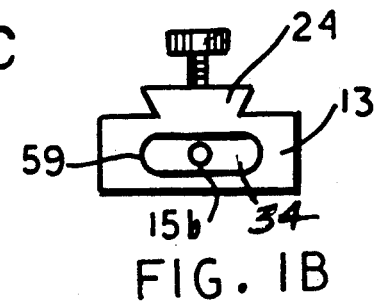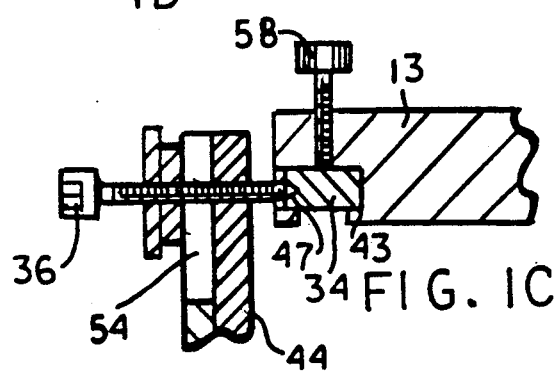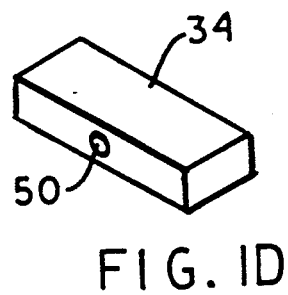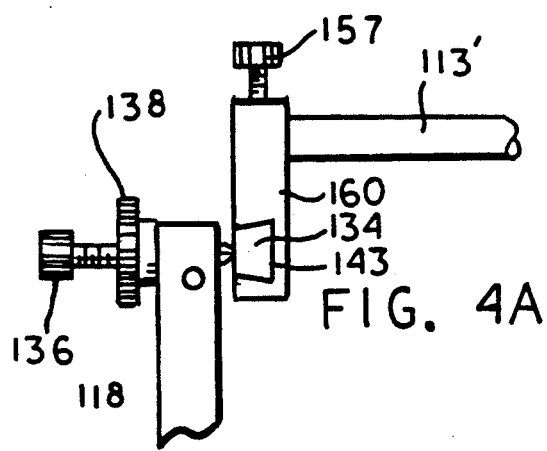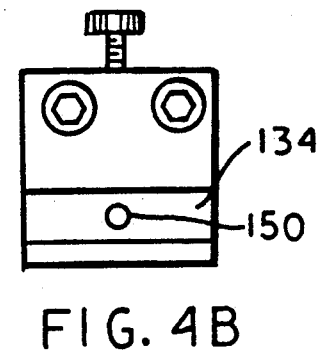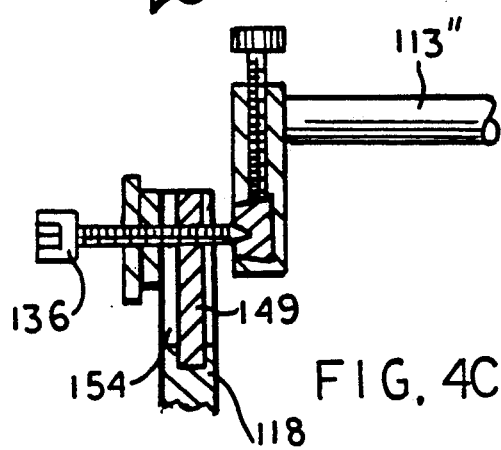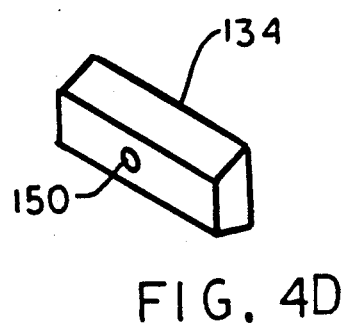

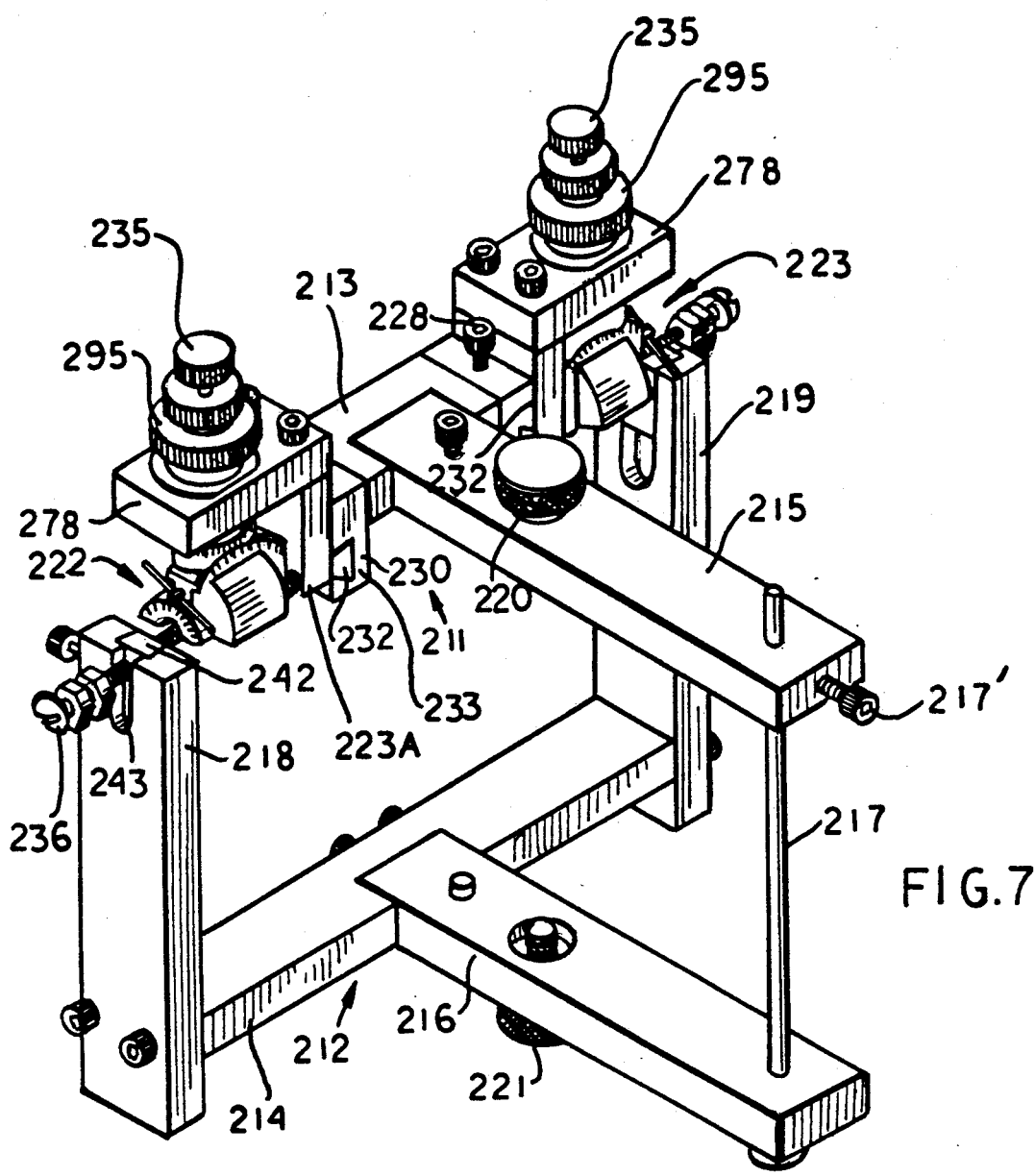
FIG. 7
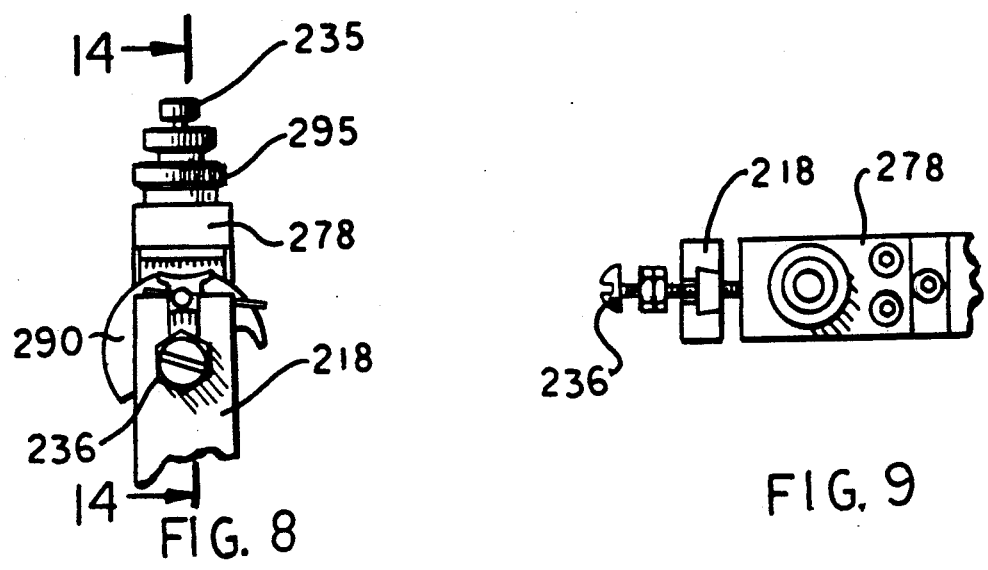
FIG. 8
FIG. 9

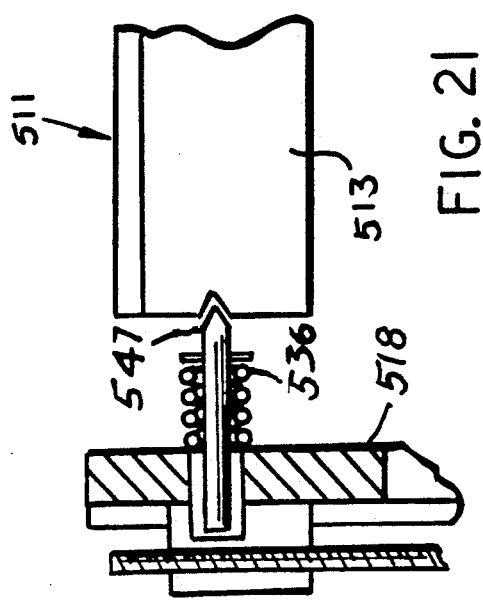
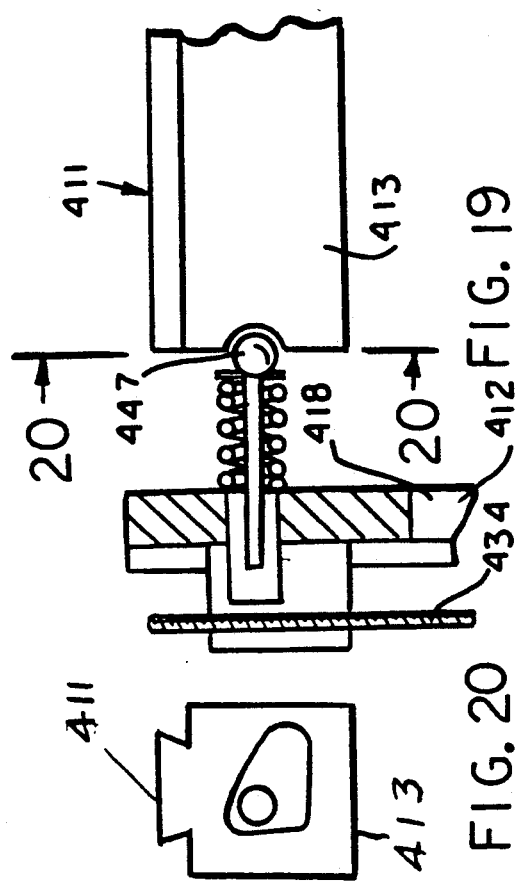

DENTAL ARTICULATOR

REFERENCE TO PRIOR ART

Dental articulators are used to simulate the jaw and jaw hinge mechanism for use in the analysis and diagnosis of dental related problems and creation of various appliances and prostheses and thereby provide according to a patient's particular bite. To accomplish this, upper and lower frame units are generally employed to simulate the upper and lower jaws. Further, condyle ball and socket arrangements are employed in a great many of these devices which were intended to correspond to the actual jaw hinges of humans. Such a device is shown in U.S. Pat. Nos. 1,033,562 to Eltner, 3,160,955 to Pietroi, 3,206,852 to Swanson, 3,409,986 to Freeman, 3,478,431 to De Pietro and applicant's prior U.S. Pat. No. 4,668,189 to Levandoski. To facilitate the description of the present invention, and to promote an understanding of the prior art of articulators in general, the aforementioned patents are referenced in the present description. It will readily appear and be understood by those skilled in the art that the present invention can be incorporated with various other articulators. This application discloses several improvements on the articulators disclosed in said patents.

The condyle ball and socket joints employed in arcon dental articulators generally provide for significant controlled adjustment to border positions to better reflect actual jaw movements. Consequently, the joints are not interlocking and will not support the upper frame when it is rotated to disengage the false teeth mounted on the articulator. As a result, it has been found useful to provide a secondary mechanism for holding the upper frame on the lower frame when the upper frame is pivoted from the engagement position. Further, the permitted relative lateral displacement of the condyle ball and sockets creates a second operational closed, occludent position when efforts are made to work on the subject teeth with both the upper and lower portions engaged.

There are two general classes of dental articulating instruments, arcon and non-arcon. The arcon articulation concept designates a mechanical feature whereby the anatomy of the jaw joints is reproduced more or less. Condylar spheres are attached to the lower beam and the fossa or condylar housings are attached to the upper beam. In the past, the articulator condyle has been provided with close and intimate contact with the fossa. This was considered necessary in order to guide the instrument to follow adjustable restraints built into the articulator in an attempt to allow reproduction of the various eccentric jaw positions and reliably return models of the jaws to a predetermined "centric" position.

Non-arcon articulators include those which incorporate the condylar spheres on the upper beam and the condylar housings in the lower beam. It has been determined that in most circumstances the arcon and non-arcon articulators produce identical results in the end, but the arcon is considered more easily understood. However, all articulator systems devised have failed to address the fact that in a large percentage of cases there is an unphysiologic relationship between the condyles and fossae which can be corrected or treated by permitting the condyle/fossa spatial relationship to be adjusted. In other words, it may be determined that a particular case may benefit from a decompression of the temporo mandibular joint space. No articulator has yet been devised which offers this possibility.

STATEMENT OF THE INVENTION

This invention relates to an apparatus for articulating models of human or animal jaw structures for the purpose of orthoenathic surgical diagnosis, fabricating prostheses, fabricating construction bites, analyzing occlusion, and diagnosing and treating temporo mandibular joint problems and discloses improvements in the construction and operation of such devices.

OBJECTS OF THE INVENTION

An object of the present invention is to provide an articulator with a range of adjustment for the decompression and/or repositioning of the condyle/fossa relationship. This dramatically simplifies diagnosis and treatment especially in cases with problems relating to malpositions or dislocations of the jaw joints.

In addition, the unique capability of this new device to be adjusted in three planes of space for each condyle allows for positive diagnosis and repositioning of patient models for reconstructive or orthoenathic jaw surgery.

Another object of the invention is to provide an articulator that is simple in construction, simple to manufacture and simple and efficient to use.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

BRIEF DESCRIPTION OF THE DRAWINGS

FIG. 1A is a partial top view of a part of the articulator shown in FIG. 1.

FIG. 1B is a longitudinal cross sectional view taken on line 1B—1B of FIG. 1A.

FIG. 1C is a cross sectional view, taken on line 1C—1C of FIG. 1A.

FIG. 1D is an isometric view of one of the blocks shown in FIG. 1.

FIG. 4A is an enlarged partial front view of a part of the invention shown in FIG. 4.

FIG. 4B is a partial end view of the upper beam shown in FIG. 4.

FIG. 4C is a longitudinal cross sectional view similar to FIG. 1C of the embodiment of FIG. 4.

FIG. 4D is an enlarged isometric view of one of the blocks shown in FIG. 4.

FIG. 7 is an isometric view of another embodiment of the invention.

FIG. 8 is a partial end view of the embodiment shown in FIG. 7.

FIG. 9 is a partial top view of the embodiment of the invention shown in FIG. 7.

FIG. 19 is an enlarged partial cross sectional view taken on line 19—19 of FIG. 17.

FIG. 20 is a cross sectional view view taken on line 20—20 of FIG. 19.

FIG. 21 is a view similar to FIG. 20 of another embodiment of the invention.

DETAILED DESCRIPTION OF THE DRAWINGS

Figure 1:
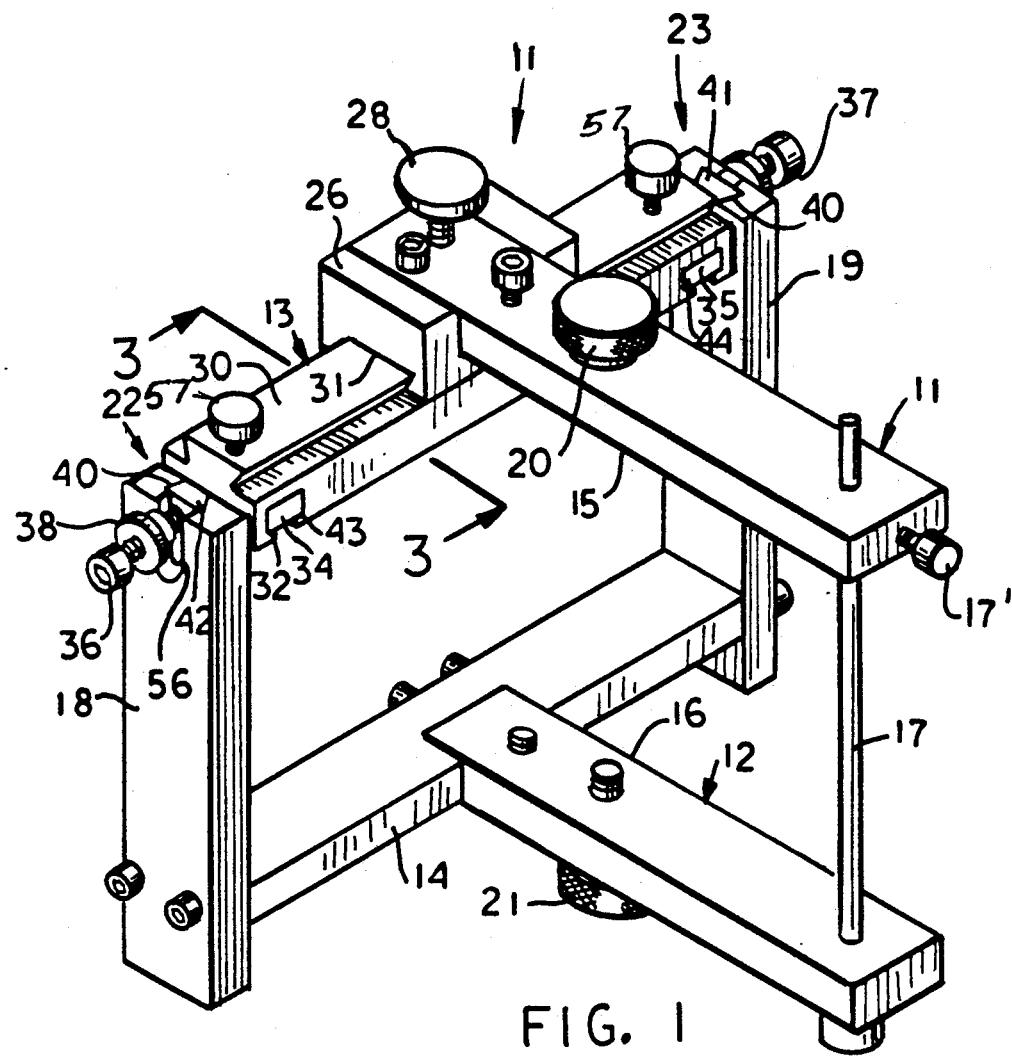
FIG. 1 is an isometric view of one embodiment of the articulator according to the invention.
Figure 2:
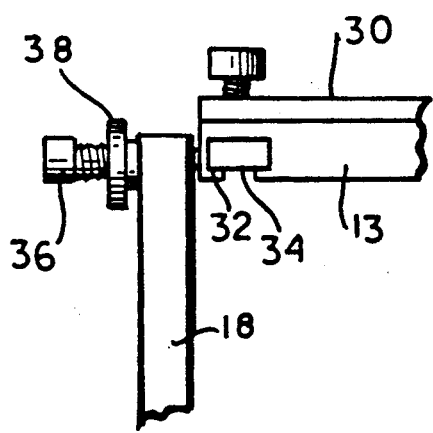
FIG. 2 is an enlarged partial front view of a part of the invention shown in FIG. 1.
Figure 3:
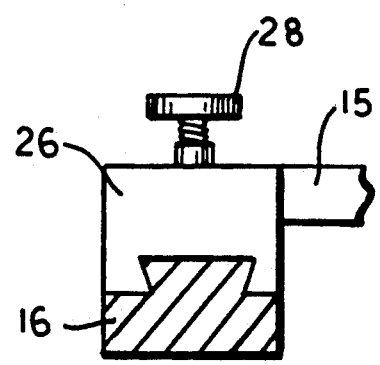
FIG. 3 is a cross sectional view taken on line 3—3 of FIG. 1.
Figure 4:
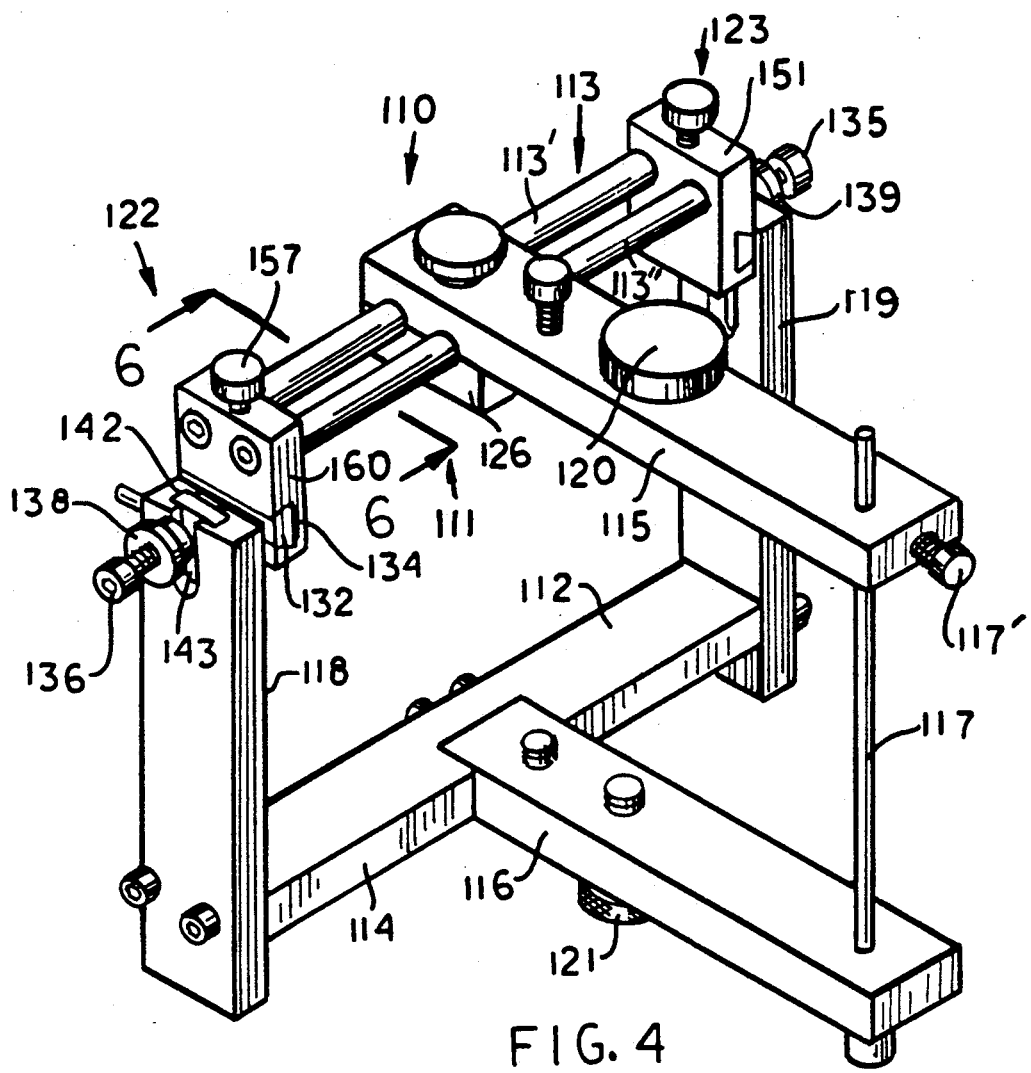
FIG. 4 is an isometric view of another embodiment of the invention.
Figure 5:
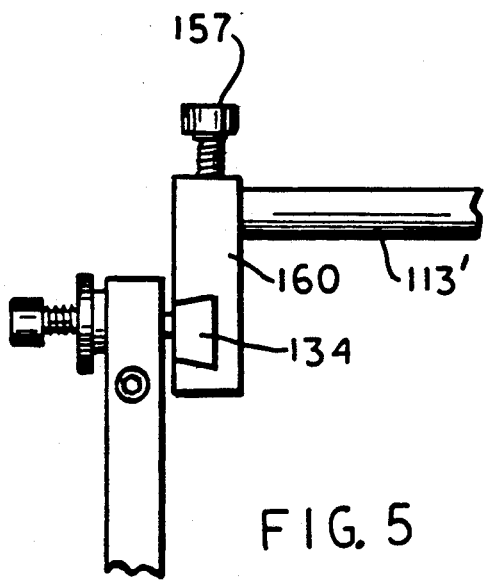
FIG. 5 is an enlarged view of a part of FIG. 4.
Figure 6:
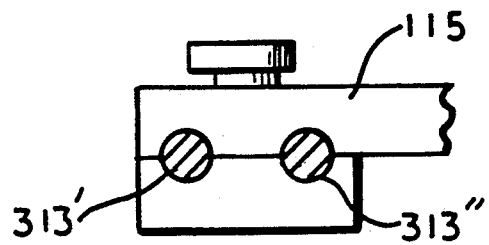
FIG. 6 is a cross sectional view taken on line 6—6 of FIG. 4.
Figure 10:
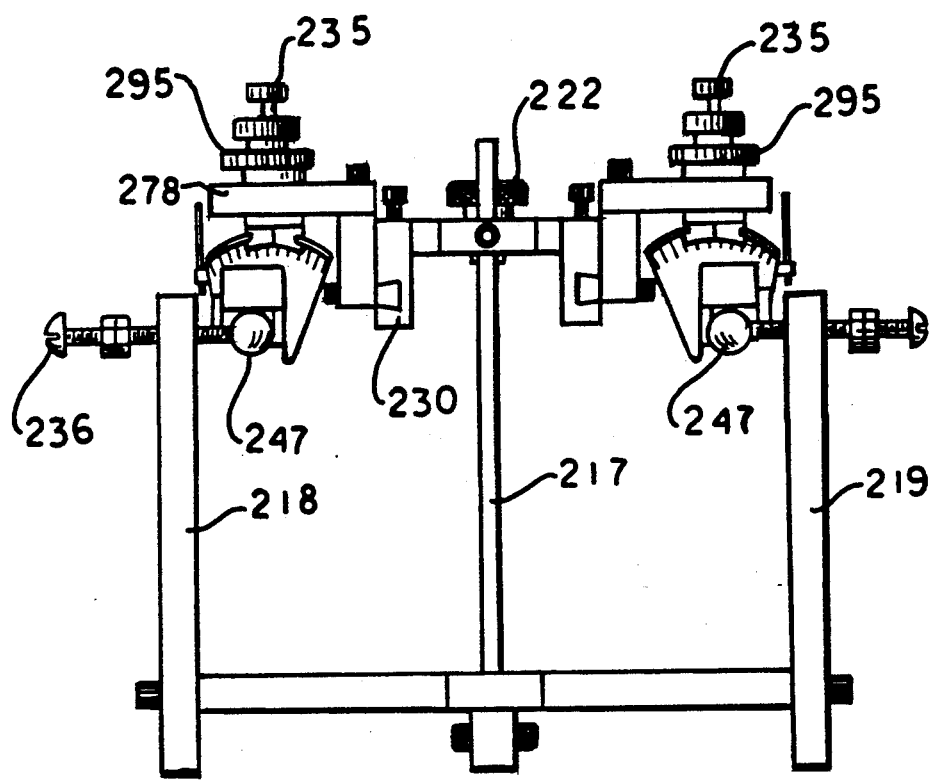
FIG. 10 is a front view of the embodiment of the invention shown in FIG. 7.
Figure 11:
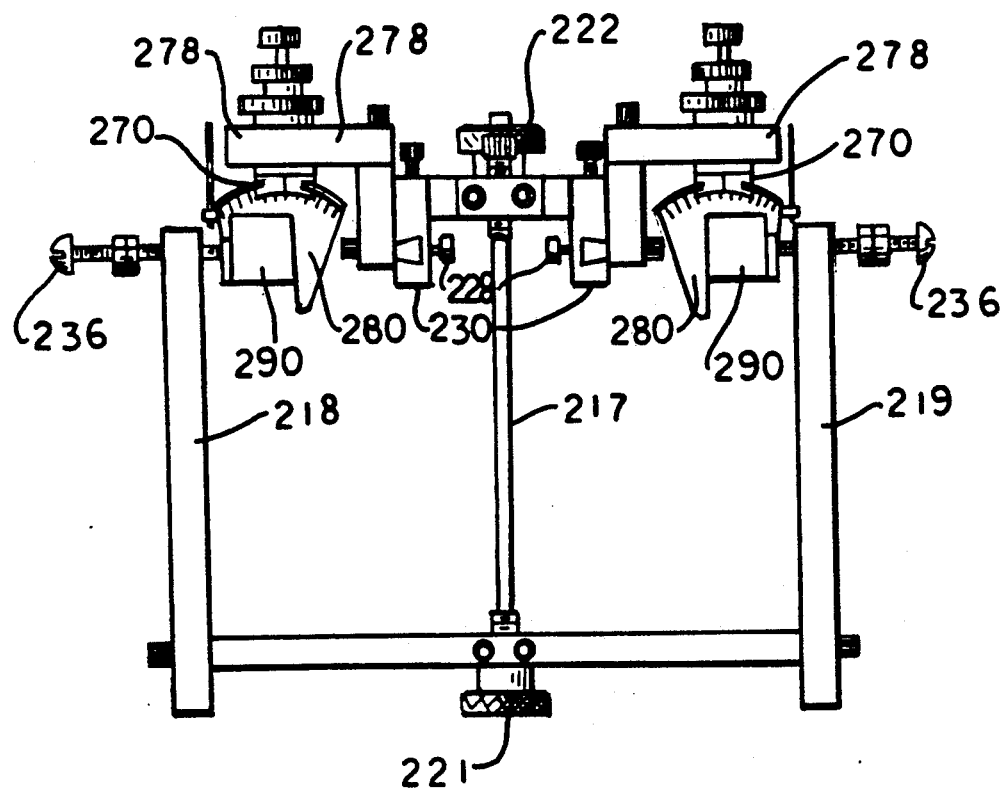
FIG. 11 is a rear view of the embodiment of the invention shown in FIG. 7.
Figure 12:
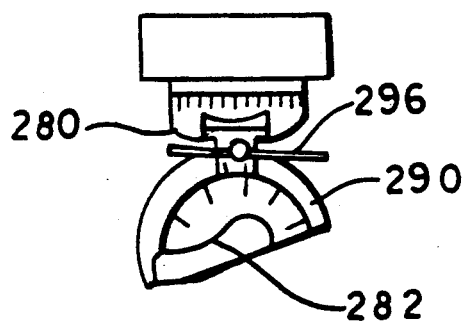
FIG. 12 is an enlarged partial end view of the embodiment of the invention shown in FIG. 7.
Figure 13:
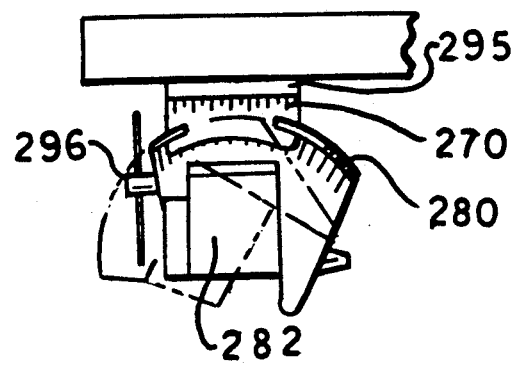
FIG. 13 is a partial front view of the embodiment of FIG. 7.
Figure 15:
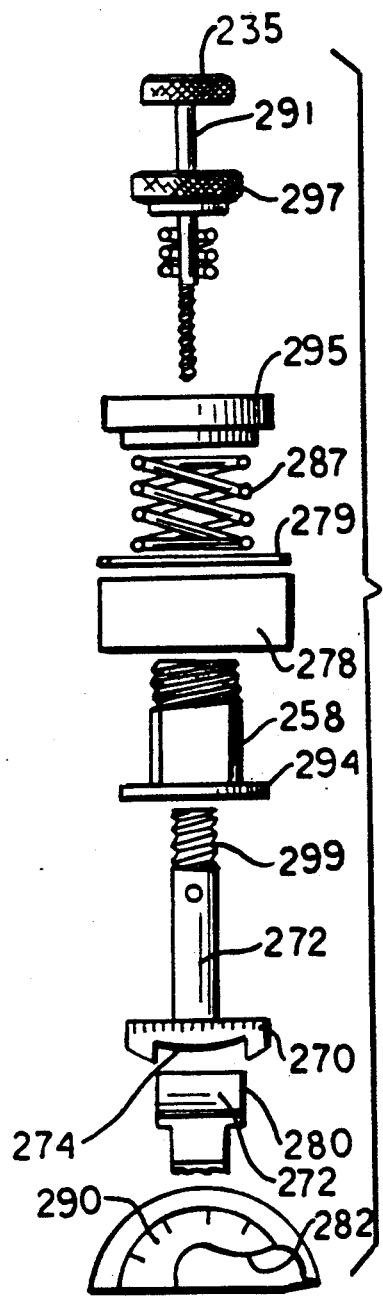
FIG. 15 is an exploded view showing the parts of the embodiment of the invention shown in FIG. 7.
Figure 14:
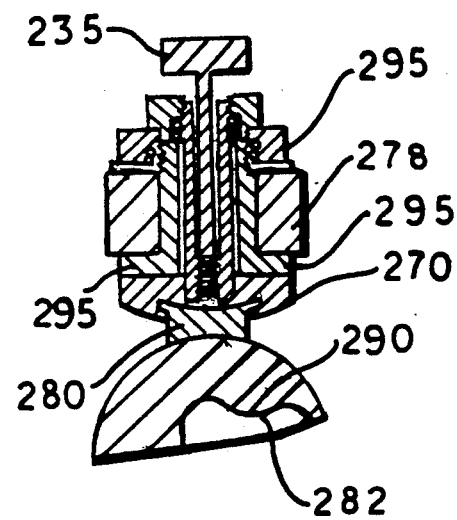
FIG. 14 is a longitudinal cross sectional view taken on line 14—14 of FIG. 8.

The embodiments of the articulator shown are improvements of the articulator shown in U.S. Pat. No. 4,668,189.

Now with more particular reference to the drawings, six embodiments of the invention are shown herein, namely, (I) the embodiment of FIGS. 1, 1A, 1B, 1C, 1D, 2, and 3; (II) the embodiment of FIGS. 4, 4A, 4B, 4C, 4D, 5 and 6; (III) the embodiment of FIGS. 7 through 15, (IV) the embodiment of FIG. 16, (V) the embodiment of FIGS. 17 through 20 and (VI) the embodiment of FIG. 21.

Referring to articulator 10 shown in embodiment I, upper frame 11 is swingably supported on lower frame 12 by first condyle connection support assembly 22 and second condyle connection support assembly 23. Upper frame 11 is made up of laterally extending upper beam 13 having intergral dovetail flange 30 which forms an downwardly facing concave surface. Dovetail flange 30 is received in dovetail slot 31 in block 26 which forms a downwardly facing concave surface. Block 26 can slide from side to side on dovetail flange 30. Block 26 can be locked in position by screw 28. Upper beam 13 has forwardly extending upper arm 15 attached thereto by block 26, dovetail flange 30 and third screw 28. Lower frame 12 has laterally extending lower beam 14. Lower beam 14 has forwardly extending lower arm 16 fixed thereto.

Incisal pin 17 is fixed to the forward end of upper arm 15. The lower end of incisal pin 17 rests on the forward end of lower arm 16 and is held in adjusted position by set screw 17'. Spaced upwardly extending first condyle post 18 and second condyle post 19 are fixed to opposite ends of lower beam 14. Upper arm 15 has a screw which acts as first denture support 20 for holding a maxillar cast. Lower arm 16 has a screw which acts as second denture support 21 for holding a lower maxillar cast.

First condyle connection support assembly 22 includes large slot 40 in first condyle post 18 which receives first dovetail slide block 42. Second condyle connection support assembly 23 includes large slot 40 in second condyle post 19 which receives second dovetail block 41. Windows 59 are formed in the ends of upper beam 13. Windows 59 provide a space for first locking screw 36 to move in upper beam 13 and communicate with first rectangular block 34. First locking screw 36 and second locking screw 37 freely slide in small slots 56.

Upper beam slots 43 and 44, in upper beam 13, receive first rectangular blocks 34 and 35. Small slot 32 communicates with upper beam slots 43 and 44. First locking screws 36 and 37 are threadably received in first dovetail slide blocks 41 and 42 and each rectangular block 34 and 35 has pivot point 47 that is received in recess 15b in first rectangular blocks 34 and 35. First lock nut 38 locks first block 42 against first condyle post 18. A similar lock nut on screw 37 locks block 41 against second condyle post 19. Pivot points 47 of first locking screw 36 provide a pivot for first dovetail slide blocks 41 and 42. It will be noted that either end of upper beam 13 can move up and down with first dovetail blocks 41 and 42 when the proper one of screws 36 and 37 are loosened, either end of upper beam 13 can slide forward with first rectangular blocks 34 and 35 when screws 57 are loosened. Upper arm 15 can pivot around pivot points 47 and swing up and down on pivot points 47. Thus upper frame 11 can pivot, tilt, and move forward or rearward relative to lower frame 12 giving an upper casting supported on second screw 20 universal adjustment relative to a lower casting supported on third screw 21.

Now with reference to the embodiment of the invention of FIGS. 4, 4A, 4B, 4C, 4D, 5 and 6, articulator 10 is shown made up of upper frame 111 and lower frame 112. Lower frame 112 is made up of laterally extending lower beam 114. Spaced upwardly extending first condyle post 118 and second condyle post 119 are fixed to the ends of lower beam 114. Lower arm 116 is fixed to lower beam 114 and extends forwardly generally perpendicular thereto. Upper frame 111 is made up of upper beam 113 and upper arm 115. Upper arm 115 has spaced downwardly facing slots 131, which form downwardly facing concave surfaces and, which receive first spaced rod 113' and second spaced rod 113" and rest on upwardly facing convex surfaces on first spaced rod 113' and second spaced rod 113". Upper beam 113, has first spaced rod 113' and second spaced rod 113", each having an upwardly facing cylindrical convex surface a first end, a second end and vertically, laterally and forwardly adjustable first condyle connection support assembly 122 and adjustable second condyle connection support assembly 123 on the respective ends supporting first spaced rod 113' and second spaced rod 113" on first condyle post 118 and second condyle post 119.

Incisal pin 117 is adjustable up and down by means of set screw 117' and the rear end of upper arm 115 is received in first slots 130 and is held to upper beam 113 by first block 126. First block 126 is clamped to upper arm 115 by screw 128. First spaced rod 113' and second spaced rod 113" each have an end secured in second block 151 and another the other end secured in third block 160. Adjustable support means includes second block 151 and third block 160 which have dovetail block 134 forwardly and rearwardly slidably received in second slots 132.

Recess 150 in dovetail block 134 receives pivot point 147 of first locking screw 136, best shown in FIG. 4C. First locking screw 136 threadably engages slide block 142 in the upper end of first condyle post 118 and second condyle post 119. First locking screw 136 freely slides in narrow slot 143 and first lock nut 138 locks first locking screw 136 in position. First lock nut 138 pulls slide block 142 against first condyle post 118 and second condyle post 119. Screw 157 locks dovetail block 134 against sliding. First lock nut 138 functions similar to first lock nut 38 in the first embodiment. In the embodiment II, block 134 is dovetail shaped and corresponds to block 34 in embodiment I which is rectangular shaped, while slide block 42 in the first embodiment is dovetail shaped and slide block 142 in the second embodiment is rectangular shaped.

Referring to the embodiment of the invention shown in FIGS. 7 through 15, upper frame 211 is swingably supported on lower frame 212 by adjustable first condyle connection support assembly 222 and adjustable second condyle connection support assembly 223. Upper frame 211 is made up of laterally extending upper beam 213. Upper beam 213 has forwardly extending upper arm 215 attached thereto. Lower frame 212 has laterally extending lower beam 214. Lower beam 214 has forwardly extending lower arm 216 fixed thereto.

Incisal pin 217 is fixed to the forward end of upper arm 215. The lower end of incisal pin 217 rests on the forward end of lower arm 216 and is held in adjusted position by set screw 217'. Spaced upwardly extending first condyle post 218 and second condyle post 219 are fixed to the ends of lower beam 214. Upper arm 215 has first screw 220 for holding a maxillar cast. Lower arm 216 has second screw 221 for holding a lower maxillar cast. Adjustable first condyle connection support assembly 222 and second condyle connection support assembly 223 are provided for adjustably supporting the ends of upper beam 213.

First flange 230 is fixed to the outer end of upper beam 213. Second flange 223A is fixed to slide block 232. Slide block 232 is slidably received in slot 233 and can slide forwardly and rearwardly in slot 233. Slide Block 232 can be locked in position by screw 228. First plate 278 is fixed to the top of second flange 223A.

First condyle connection support assembly 222 and second condyle connection support assembly 223 are similar to the condyle adjustment shown in U.S. Pat. No. 3,160,955 except Applicant's first and second condyle assemblies contains one additional element (second cylindrical guide 280) which makes it possible to achieve greater accuracy. First condyle connection support assembly 222 and second condyle connection support assembly 223 are made up of a cam arrangement made of first cylindrical guide 270, second cylindrical guide 280, and third cylindrical guide 290. The axis of rotation of first cylindrical guide 270 is disposed at right angles to the axis of rotation of second cylindrical guide 280. First condyle connection support assembly 222 and second condyle connection support assembly 223 are similar to the adjusting mechanism corresponding to the adjusting mechanism shown in FIGS. 1 and 4 herein except that upper beam 213 has first flange 230 attached to its ends. Slot 233 receives slide block 232 and are similar to the corresponding block 134 in the second embodiment. First locking screw 236 and first lock nut 238 are received in third cylindrical guide 290. Cam surface 282 on third cylindrical guide 290 forms a seat for condyle ball 247 to slide on. Cam surface 282 simulates the human fossa. Second cylindrical guide 280 is received in cylindrical slot 274 in first cylindrical guide 270.

First cylindrical guide 270 has threaded pin 272 attached thereto threadably engaging first nut 295 and adapted to pull first cylindrical guide 270 into frictional engagement with second plate 294 against the force of spring 287. Thus, first cylindrical guide 270 can rotate relative to first plate 278 against the frictional force exerted by first nut 295 through spring 287. External cylindrical guide surface 272' can be locked relative to first guide surface 274 by second threaded pin 291 which has head 235 on it. Second threaded pin 291 is threaded into first pin 272 and when tightened engages surface 272'. Second nut 297 is threadably supported on threaded ends 299 of first pin 272. Second cylindrical guide 280 has internal cylindrical surface 286 which slidably engages external surface 292 on third cylindrical guide 290. Third cylindrical guide 290 is locked into position by second pin 291. First cylindrical guide 270, second cylindrical guide 280 and third cylindrical guide 290 are all supported in contact with one another. Therefore, it will be seen that by adjusting these members relative to each other condyle ball 247 is brought into different relation to cam surface 282. Upper beam 213 and lower beam 212 can be adjusted and swung upwardly relative to one another through a variety of complex positions.

Figure 16:
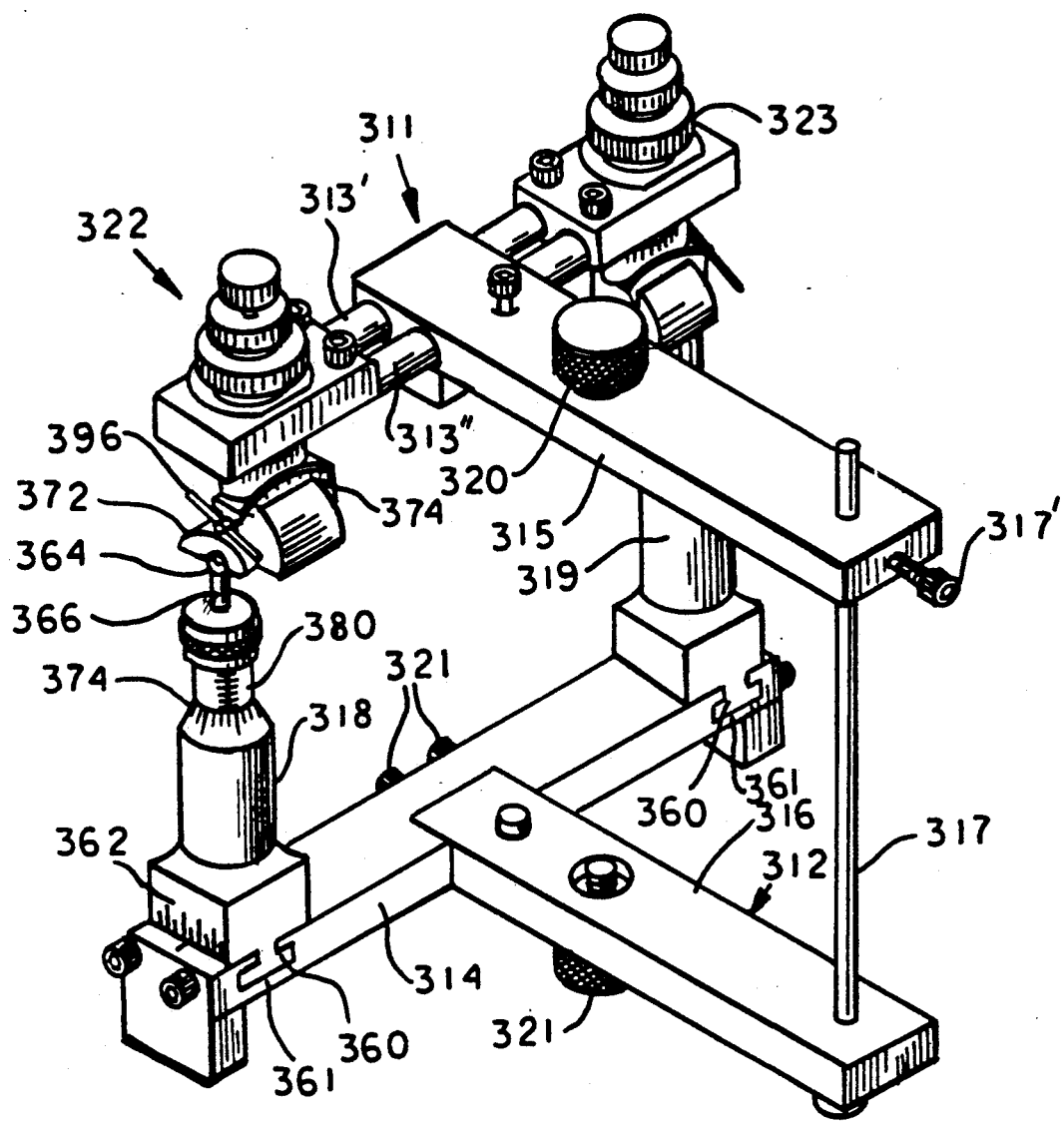
FIG. 16 is an isometric view of another embodiment of the invention.

Referring to the embodiment of the invention shown in FIG. 16, upper frame 311 is swingably supported on lower frame 312 by first condyle support assembly 322 and second condyle support assembly 323. Upper frame 311 is made up of laterally extending upper beam 313. Upper beam 313 has forwardly extending upper arm 315 attached thereto. Lower frame 312 has laterally extending lower beam 314. Lower beam 314 has forwardly extending lower arm 316 fixed thereto.

Incisal pin 317 is fixed to the forward end of upper arm 315. The lower end of incisal pin 317 rests on the forward end of lower arm 316 and is held in adjusted position by set screw 317'. Spaced upwardly extending first condyle post 318 and second condyle post 319 are slidably supported on the ends of lower beam 314 by T-shaped tongues 360 received in slots 361. Upper arm 315 has first screw 320 for holding a maxillar cast. Lower arm 316 has second screw 321 for holding a lower maxillar cast. Adjustable first condyle support assembly 322 and adjustable second condyle support assembly 323 are provided for adjustably supporting the ends of upper beam 313 and are similar to the corresponding parts of FIGS. 7 through 15. Micrometer screws 380 are threadably received in first condyle post 318. Condyle balls 364 engage a condyle surface on cylinder 372 locked by screw 396.

Figure 17:
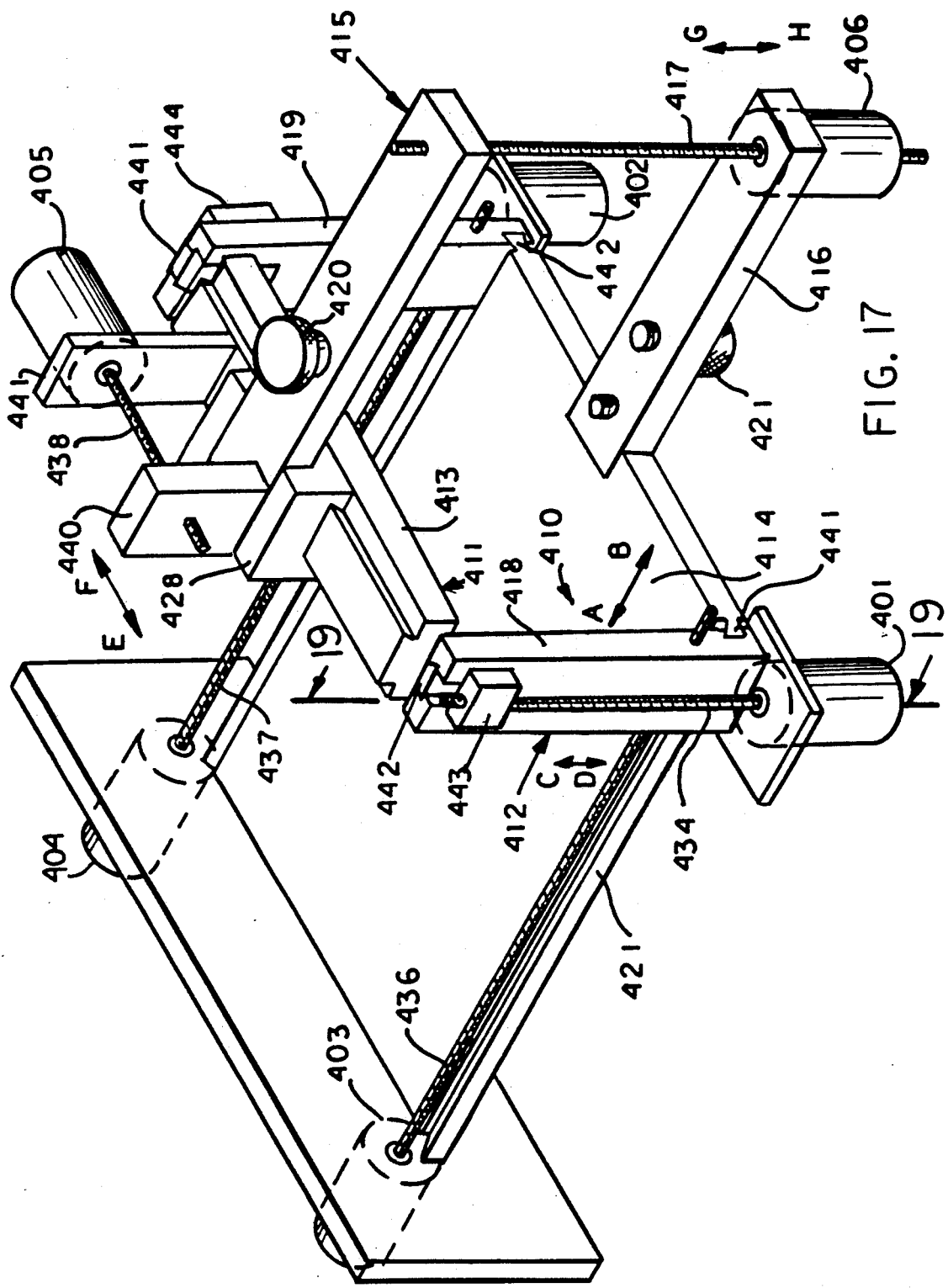
FIG. 17 is a schematic view of another embodiment of the invention including motors and gearing for operating the articulator from a computerized source shown in FIG. 18.
Figure 18:
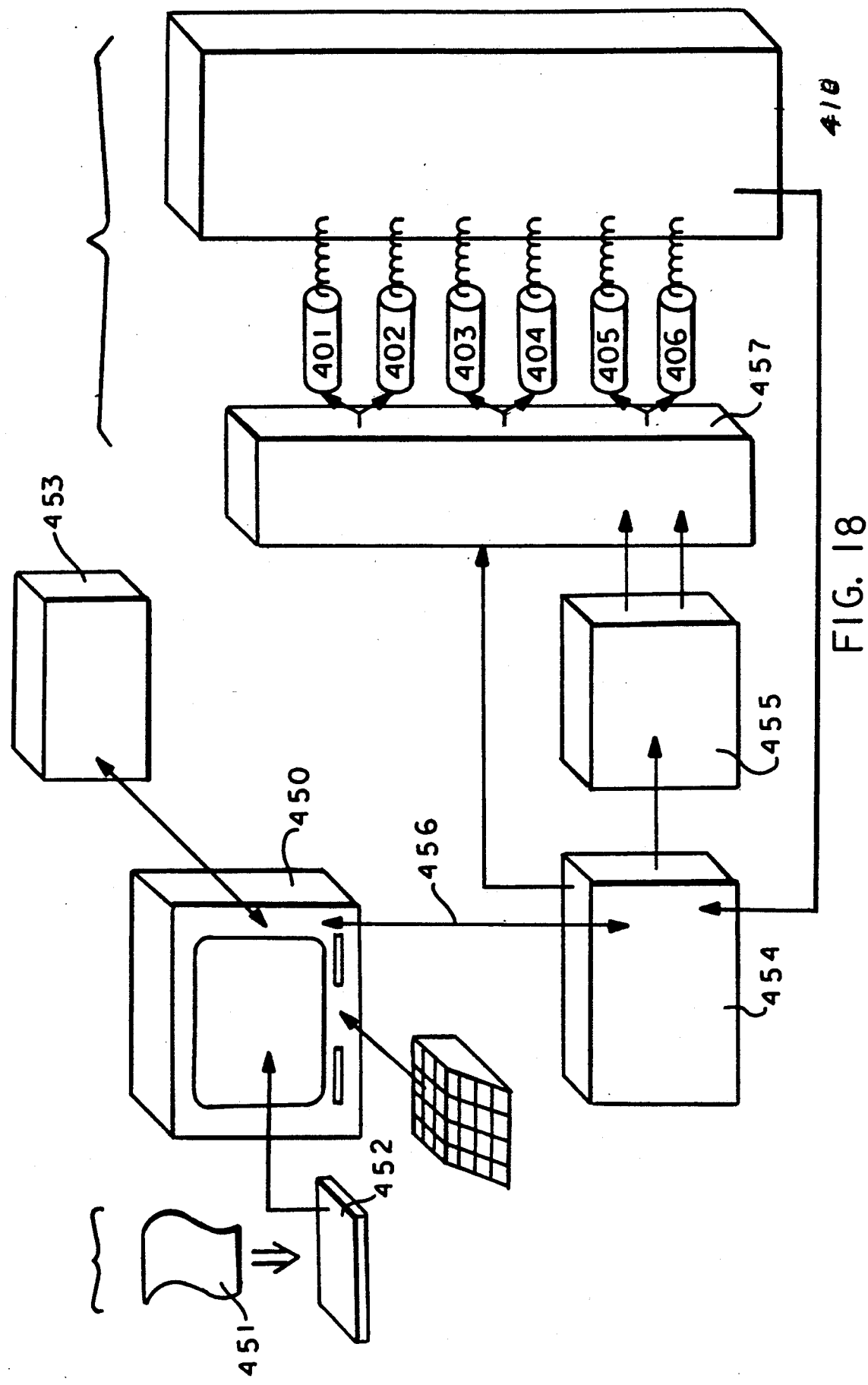
FIG. 18 is a block diagram of a computer system for operating the articulator shown in FIG. 17.

Now with more particular reference to the embodiment of the invention shown in FIGS. 17 and 18, articulator 410 comprises upper frame 411 and lower frame 412. Upper frame 411 is made up of upper beam 413 having upper arm 415 attached thereto and extending forwardly therefrom. Incisal pin 417 threadably engages upper arm 415 and extends downwardly therefrom. First support or model ring 420 may be attached to a dental mounting plate and fixed to upper arm 415. Second screw 421 may have a dental mounting plate fixed thereto.

Lower frame 412 is made up of laterally extending lower beam 414 having a first end and a second end. Lower arm 416 is fixed to lower beam 414 and extends forwardly generally parallel to upper arm 415. Lower beam 414 has upwardly extending first condyle post 418 and second condyle post 419 slidably supported on its ends. First slider joint 441 and second slider joint 442 are slidably received in the lower ends of first condyle post 418 and second condyle post 419. In the examples shown, first slider joint 441 and second slider joint 442 are dovetail shaped but they could be of different shapes such as T-shaped, cylindrical or square. First nut 443 and second nut 444 are attached to the ends of upper bam 413 through second slider joint 442.

Motors 401, 402, 403, 404, 405 and 406 are provided each connected to lead screws 434, 436, 437, 438 and incisal pin 417 respectively to move upper arm 415 relative to lower arm 416. The purpose of motor 401 is to rotate screw 434 to a prescribed angle in a clockwise or counter-clockwise rotation, thereby moving internally threaded first nut 443 upward and downward in the direction of arrow C-D. Motors 403 and 404 move first condyle post 418 and second condyle post 419 forward and rearward relative to lower beam 414. Motor 405 slides block 440 laterally in accordance with information fed to it, by a circuit, as shown in FIG. 18, as well as information fed to the other motors by the circuit shown in FIG. 18. Motor 406 swings upper arm 415 on condyle pivots 447 which support upper beam 413.

The block diagram of FIG. 18 shows a circuit in which data in the form of vectors, is generated within a computer program to accurately represent deviations from a typical jaw. The vectors describe the dysfunction of the disordered jaw which is to be treated. The circuit includes the addition of transducers and electronic circuitry to faithfully represent the vectors into physical displacements of the simulation apparatus. The apparatus has been shown in various embodiments elsewhere in this disclosure.

FIG. 17 shows a modification of articulator 410 so as to include motors 401 through 406 and appropriate structure for interfacing those motors with articulator 410. Motors 401 through 406 rotate through an angle of 1.8° for each pulse from the circuit shown in FIG. 18.

A forward-backward motion is achieved by using motor 403 to rotate screw 436 which is threaded into a hole in first condyle post 418. As screw 436 is rotated by motor 403 it causes first condyle post 418 to move in the directions A-B, thereby providing the forward-backward motion of first condyle post 418 and the first end of upper beam 413. First condyle post 418 has a key way milled into its side, such that first condyle post 418 engages lower beam 414, and second condyle post 419 can slide along the edge of lower beam 414. A like arrangement is provided at the other side, where motor 404 provides the same motion for that end of lower beam 414.

Lateral motion along upper beam 413 is provided by motor 405 which rotates screw 438 that engages a threaded hole in block 440, causing block 440 to move in the directions E-F. Block 440 is attached to upper arm 415, and therefore, upper arm 415 moves with block 440.

Electronics, software, and control are shown in FIG. 18. Central to the operation is computer 450. X-ray 451 is placed on input tablet 452, which records data from X-ray 451 for processing by computer 450. As described previously, computer 450 generates vectors for the adjustment of motors 401 through 406 on articulator 410. Software program 453 provides interpretation and scaling of the vectors in view of particular ratios and dimensions within the particular apparatus.

Input-output board 454 carries control information out to motors 401 through 406 and also accepts inputs from limit switches and centering indicators located on articulator 410. Input-output board 454 output is boosted in power by dual stepper-motor drivers 455. A second group of output lines from input-output board 454 selects the particular pair of motors that is to be operated at that instant, and reed relays 457 interpret this selection process to direct the appropriate drivers to the appropriate motors 401 through 406. Reed relays 457 allow multiplexing of motors 401 through 406 onto dual drives 455 for economy.

FIG. 18 further shows schematically that motors 401 through 406 are connected to articulator 410 and that limit, centering and position information is taken from articulator 410 and fed back to input-output board 454. Observe that input-output board 454 is connected to computer 450 by two-ended arrow 456, to show that there is a two-way flow of information and control signal.

FIGS. 19 and 20 show a spring loaded condyle pivot 447 supporting upper beam 413 to compensate for the increase in distance between first condyle post 418 and second condyle post 419 when they are moved relative to lower beam 414.

FIG. 21 shows another embodiment similar to FIGS. 19 and 20 which includes condyle point 547 spring loaded by spring 536 on first condyle post 518, which urges condyle point 547 into engagement with upper beam 513 of upper frame 511.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. An articulator comprising an upper frame and a lower frame,
   said upper frame being swingably supported on said lower frame to swing about a horizontal axis about pivot means,
   said lower frame comprising a laterally extending lower beam,
   spaced upwardly extending first condyle post and second condyle post supported on said laterally extending lower beam,
   a lower arm supported on said lower beam and extending forwardly and generally perpendicular thereto,
   said upper frame comprising an upper beam,
   said upper beam having a first end and a second end,
   an upper arm,
   a laterally adjustable support means laterally slidably supporting said upper arm on said upper beam,
   said laterally adjustable support means comprising a laterally extending downwardly facing concave surface on said upper arm and a laterally extending upwardly facing convex surface on said upper beam, said downwardly facing concave surface resting on said convex surface slidably supporting said upper arm on said upper beam received in said concave surfaces, a vertically adjustable first condyle support assembly supporting said first end of said upper beam on said first condyle post for adjusting each said end of said upper beam vertically relative to said first condyle post and said second condyle post, a vertically adjustable second condyle support assembly supporting said second end of said upper beam on said second condyle post.

2. The articulator recited in claim 1 wherein said upper beam comprises two spaced parallel rods having a first end and a second end, a first block supported on said first end of a said rod and a second block supported on said second end of a said rod, a support means on said condyle posts supporting said first end of said upper beam on said first condyle post and said second end of said upper beam on said second condyle post.

3. The articulator recited in claim 1 wherein said upper beam is supported on said first condyle post and said second condyle post by means of a first condyle ball on said first condyle post and a second condyle ball on said second condyle post, said upper beam having a first cylindrical guide on said first end of said upper beam and a second cylindrical guide on said second end of said upper beam, said first condyle ball engaging said first cylindrical guide and said second condyle ball engaging said second cylindrical guide.

4. The articulator recited in claim 1 wherein an electrical actuating motor is connected to said laterally adjustable support means.

5. The articulator recited in claim 4 wherein said vertically adjustable first condyle support assembly and said vertically adjustable second condyle support assembly comprise motor means.

6. The articulator recited in claim 5 wherein a computer means is connected to said motor means, said computer means is adapted to receive X-ray information of a patient's jaw structure.

7. The articulator recited in claim 6 wherein said first condyle post and said second condyle post are slidably supported on said lower beam.

8. The articulator recited in claim 1 wherein said first condyle post and said second condyle post are slidably supported on said lower beam.

9. The articulator recited in claim 1 wherein said adjustable support means includes clamping means to clamp said convex surface to said concave surface for holding said arm on said beam in an adjusted position.

10. An articulator comprising an upper frame and a lower frame, said upper frame being swingably supported on said lower frame to swing about a horizontal axis about pivot means, said lower frame comprising a laterally extending lower beam, spaced upwardly extending first condyle post and second condyle post supported on said laterally extending lower beam, a lower arm supported on said lower beam and extending forwardly and generally perpendicular thereto, said upper frame comprising an upper beam, said upper beam having a first end and a second end, an upper arm, a laterally adjustable support means laterally slidably supporting said upper arm on said upper beam, a vertically adjustable first condyle support assembly supporting said first end of said upper beam on said first condyle post for adjusting each said end of said upper beam vertically relative to said first condyle post and said second condyle post, a vertically adjustable second condyle support assembly supporting said second end of said upper beam on said second condyle post, said upper beam comprises a dovetail flange integrally attached to the top of said upper beam extending generally from end to end thereof, said laterally adjustable support means on said upper beam comprises a block, said block having a dovetail shaped slot slidably receiving said dovetail flange, a locking means on said block to lock said upper arm in a laterally adjusted position on said upper beam.

11. The articulator recited in claim 10 wherein said upper beam comprises a first rod and a second rod, said upper arm has a plurality of slots, said first rod and said second rod are slidably received in said slots in said upper arm, a locking means on said upper arm for locking said upper arm against sliding in said slots on said upper beam.

12. The articulator recited in claim 10 wherein said first condyle support assemby and said second condyle support assembly comprises condyle balls supported on a threaded screw, a first cylindrical guide supported on said upper beam engaging said condyle balls.

13. The articulator recited in claim 10 wherein said first condyle support assembly comprises a vertically extending first large slot in said first condyle post, a vertically extending second large slot in said second condyle post, a first vertically extending small slot in said first condyle post communicating with said first large slot, a second vertically extending small slot in said second condyle post, said first vertically extending small slot and said second vertically extending small slot joining said first large slot and said second large slot respectively, a first block slidably received in said first large slot, a first locking screw threadably received in said first block, pivot means on said first locking screw engaging said first block and said second block on said upper beam whereby said upper beam is pivotally supported on said first condyle post and on said second condyle post.

14. The articulator recited in claim 13 wherein said condyle connection support assemblies further comprise a horizontally and forwardly extending large slot in a first end of said upper beam, a horizontally and forwardly extending first large slot in a second end of said upper beam, a horizontally and forwardly extending first small slot in said upper beam communicating with said second large slot, a first beam block received in said horizontally and forwardly extending first large slot, a second beam block slidably received in said second horizontally and forwardly extending large slot, said screw on said first condyle post engaging said first beam block and said first beam block providing a pivot for said upper beam.

15. The articulator recited in claim 14 wherein a first small slot is formed in said upper beam joining said second large slot and said screw is freely movable in said small slot.

16. The articulator recited in claim 10 wherein said laterally adjustable support means comprises a first block and a second block, said upper beam comprises two spaced parallel rods each having a first end and a second end, said first end of each said rod being fixed to said first block, said second end of each said rod being fixed to said second block.

17. An articulator comprising a first frame and a second frame, a first pivot means and a second pivot means spaced from said first pivot means connecting said first frame to said second frame, said first frame comprising a forwardly extending upper beam, first denture support means supported on said forwardly extending beam, second denture support means supported on said second frame, a first motor means connected to said first frame and to said second frame to swing said forwardly extending beam on said pivot means in a vertical plane relative to said first frame whereby said first denture support means and said second denture support means are swung in a vertical plane relative to one another, a second motor means connected to said first frame and to said second frame adapted to swing said first frame and said second frame relative to one another in a horizontal plane whereby said first denture support means is rotated in a horizontal plane relative to said second denture support means, a third motor means connected to said first frame and said second frame to swing said first frame about said first pivot means and said second pivot means, a fourth motor means connected to said forwardly extending beam and to said first frame to move said forwardly extending beam laterally relative to said said second frame.

18. A method of articulating dental models providing an articulator comprising a first frame and a second frame, pivot means comprising condyle means connecting said first frame to said second frame whereby said first frame will swing about a horizontal axis relative to said second frame, first denture support means on said first frame, second denture support means on said second frame, (a) determining by clinical examination, radiographic evaluation including a transcranial radiograph and past history whether the patient requires condylar repositioning or decompression, (b) determining a corrected condylar position by superimposing a second condylar tracing in a position to give the desired displacement, (c) determining the difference in position of the two points and converting them to vertical and horizontal components, (d) providing a computer program capable of generating vectors which represent said differences in position of said two points from a typical jaw whereby said vectors represent the dysfunction of said jaw, (e) providing an articulator for supporting said denture relative to one another with means to rotate said dentures relative to one another in a horizontal plane, in a vertical plane to move said dentures relative to one another laterally and longitudinally and to swing said dentures relative to one another and, (f) connecting transducers electronics and software to said articulator articulating said articulator and articulating said dentures, (g) repositioning the styluses vertically and horizontally to obtain the same relationship between the upper and lower beams of the instrument whereby the models previously mounted on the articulator are positioned to a corrected therapeutic position which reflects the clinical and radiographically determined position, (h) adjusting the threaded styluses to provide a horizontal adjustment in cases where a midline correction is required.

19. An articulator comprising an upper frame and a lower frame, said upper frame being swingably supported on said lower frame to swing about a horizontal axis about pivot means, said lower frame comprising a laterally extending lower beam, spaced upwardly extending first condyle post and second condyle post supported on said laterally extending lower beam, a lower arm supported on said lower beam and extending forwardly and generally perpendicular thereto, said upper frame comprising an upper beam, said upper beam having a first end and a second end, an upper arm, a laterally adjustable support means laterally slidably supporting said upper arm on said upper beam, a vertically adjustable first condyle support assembly supporting said first end of said upper beam on said first condyle post for adjusting each said end of said upper beam vertically relative to said first condyle post and said second condyle post, a vertically adjustable second condyle support assembly supporting said second end of said upper beam on said second condyle post, said first condyle post and said second condyle post are horizontally slidable on said lower beam, a first motor means is supported on said lower beam, a driver means connected to said first motor means and to a second motor means for adjusting said first condyle post and said second condyle post horizontally on said lower beam.

20. The articulator recited in claim 19 wherein said first vertically adjustable support assembly comprises a second motor means connected to said upper frame and to said lower frame.

21. The articulator recited in claim 20 wherein a third motor means is supported on said upper frame and connected to said upper arm for laterally moving said upper arm on said upper beam.

22. The articulator recited in claim 21 wherein a fourth motor means is connected to said upper arm and supported on said lower frame for swinging said upper arm about said pivot point.

23. The articulator recited in claim 22 wherein computer means is provided, said computer means being connected to said motors.

* * * * *